US007186979B1

(12) United States Patent
Wong

(10) Patent No.: US 7,186,979 B1
(45) Date of Patent: *Mar. 6, 2007

(54) PASSIVE NDIR CARBON DIOXIDE SENSOR FIRE DETECTOR

(75) Inventor: Jacob Y. Wong, Goleta, CA (US)

(73) Assignee: Airware, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/317,266

(22) Filed: Dec. 23, 2005

Related U.S. Application Data

(63) Continuation-in-part of application No. 11/284,460, filed on Nov. 21, 2005.

(51) Int. Cl.
G01N 21/35 (2006.01)

(52) U.S. Cl. .............. 250/336.1; 250/339.15; 250/339.13; 250/339.01; 250/339.12; 340/328; 340/627; 340/629

(58) Field of Classification Search ........... 250/339.15, 250/339.3
See application file for complete search history.

(56) References Cited

U.S. PATENT DOCUMENTS

| 5,486,810 A | * | 1/1996 | Schwarz ........... 340/521 |
| 5,721,430 A | * | 2/1998 | Wong ............. 250/339.13 |
| 5,800,360 A | * | 9/1998 | Kisner et al. ........... 600/532 |
| 5,966,077 A | * | 10/1999 | Wong ............. 340/630 |
| 6,166,647 A | * | 12/2000 | Wong ............. 340/628 |
| 2005/0092067 A1 | * | 5/2005 | Petrovic et al. ........... 73/31.05 |

* cited by examiner

Primary Examiner—David Porta
Assistant Examiner—Djura Malevic
(74) Attorney, Agent, or Firm—Wagner, Anderson & Bright, LLP; Roy L. Anderson

(57) ABSTRACT

A fire detector with a passive $CO_2$ sensor generates a detector signal based upon a 15μ absorption band of $CO_2$ and a signal processor generates an alarm signal when a preselected criterion is met. The passive $CO_2$ sensor has a passive infrared source with a source temperature, a waveguide sample chamber with a gas medium temperature (which is less than the source temperature), a heat exchanger (that reduces the temperature of $CO_2$ gas as it passes into the waveguide sample chamber and may be thermally coupled to the sample chamber) and an infrared detector assembly with a detector temperature (which is less than the source temperature). An exterior surface of the passive infrared source has a high emissivity while the detector assembly and the sample chamber (which can be thermally coupled to each other but not the passive infrared source) have a low emissivity.

17 Claims, 6 Drawing Sheets

A schematic design and implementation of a passive NDIR CO2 sensor without the use of an active radiation source and deployed as a low power fire detector.

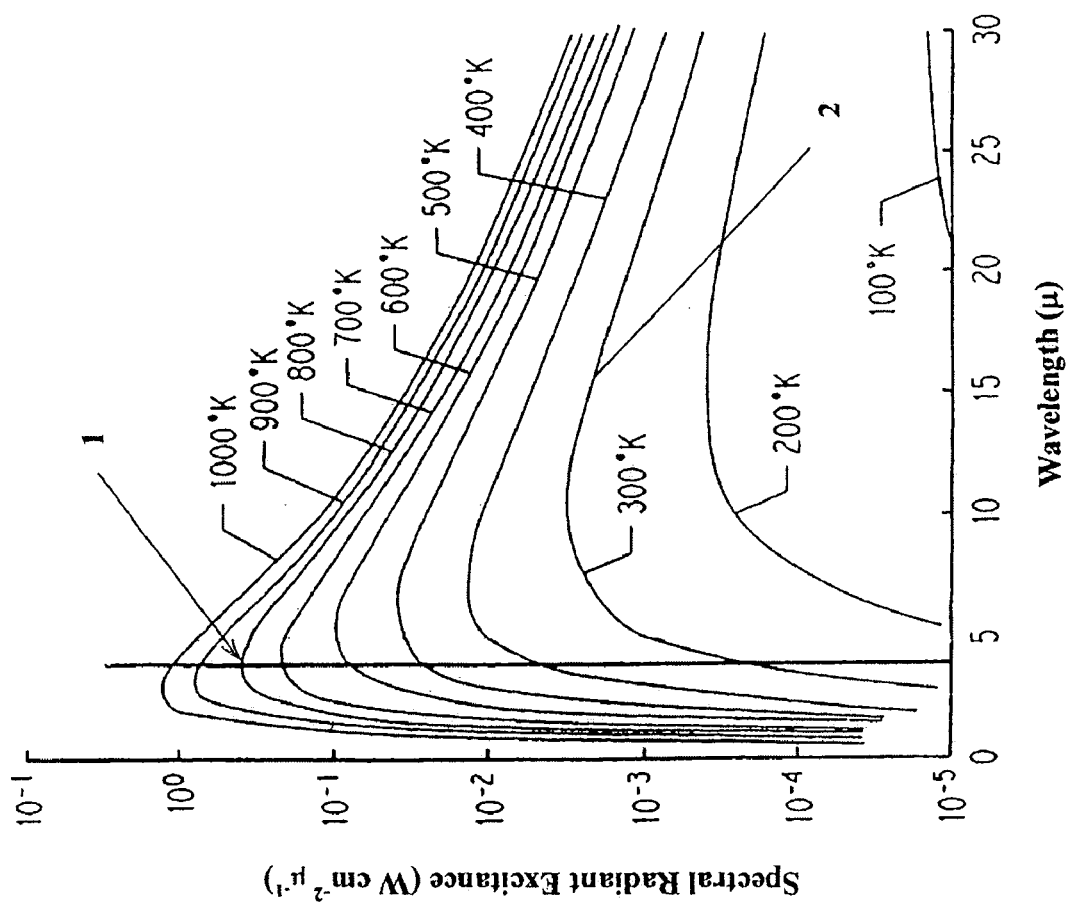
Figure 1. A graph showing the spectral radiant excitance of a blackbody source at temperatures 100 - 1,000 °K.

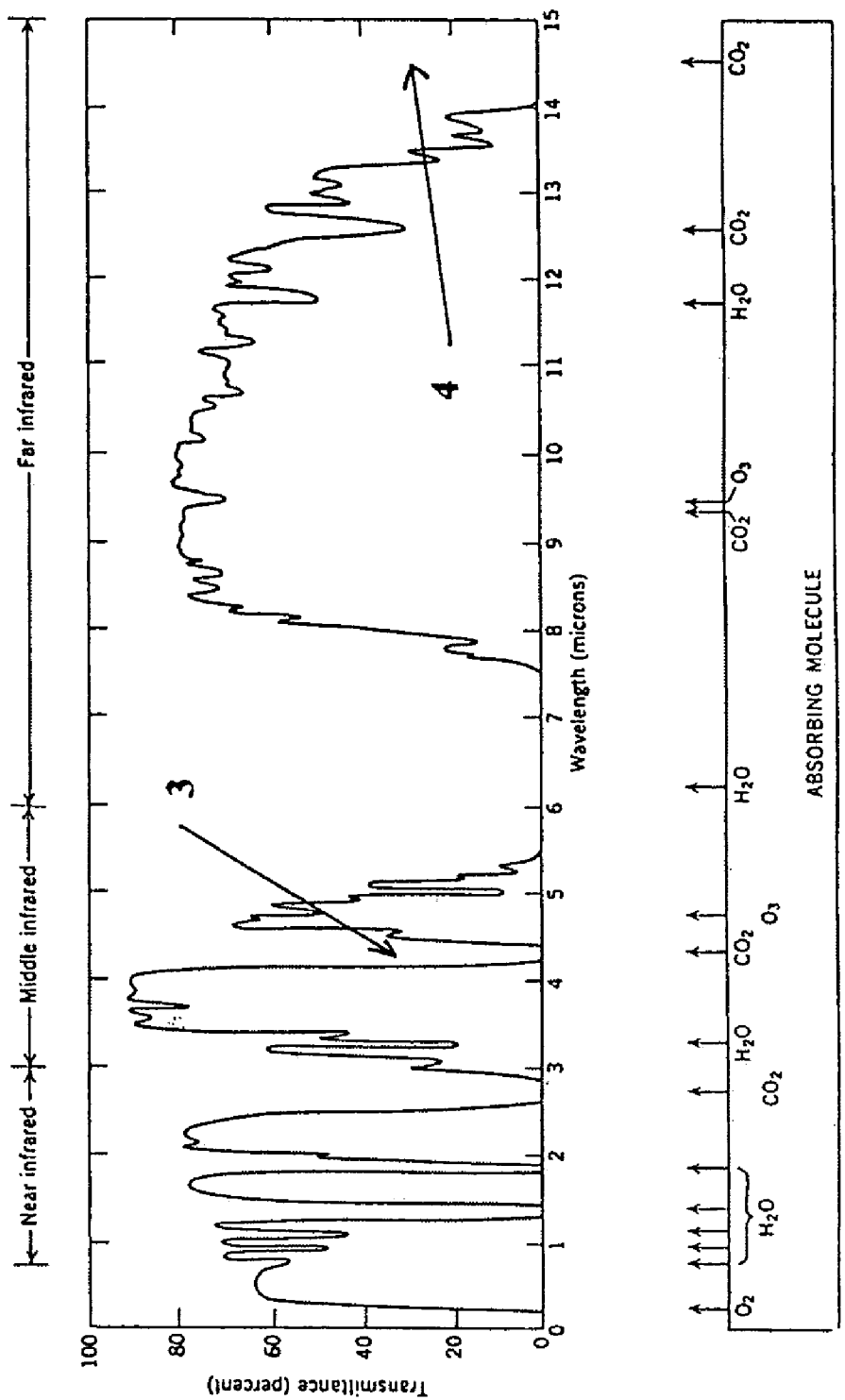
Figure 2. The transmittance of the atmosphere for a 6,000 ft. horizontal path at sea level showing the presence of the $CO_2$ absorption bands at 4.26μ and ~15μ.

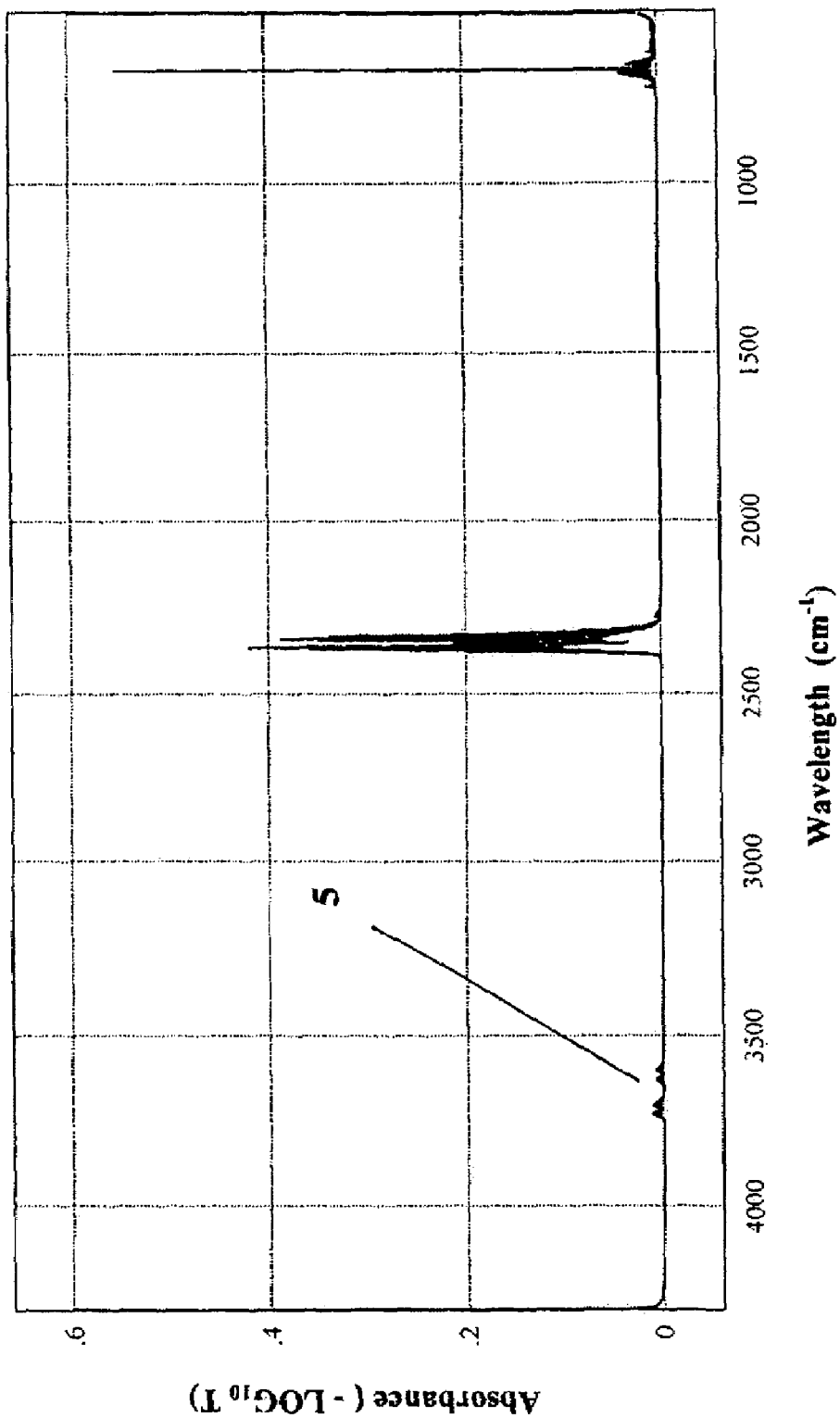
Figure 3. A schematic graph showing the absorbance of CO2 gas at wavelengths from 2μ – 20μ (5,000 cm$^{-1}$ – 500 cm$^{-1}$). Only the 4.26μ and ~15μ absorption bands of CO2 are shown to be prominently present in this spectral region.

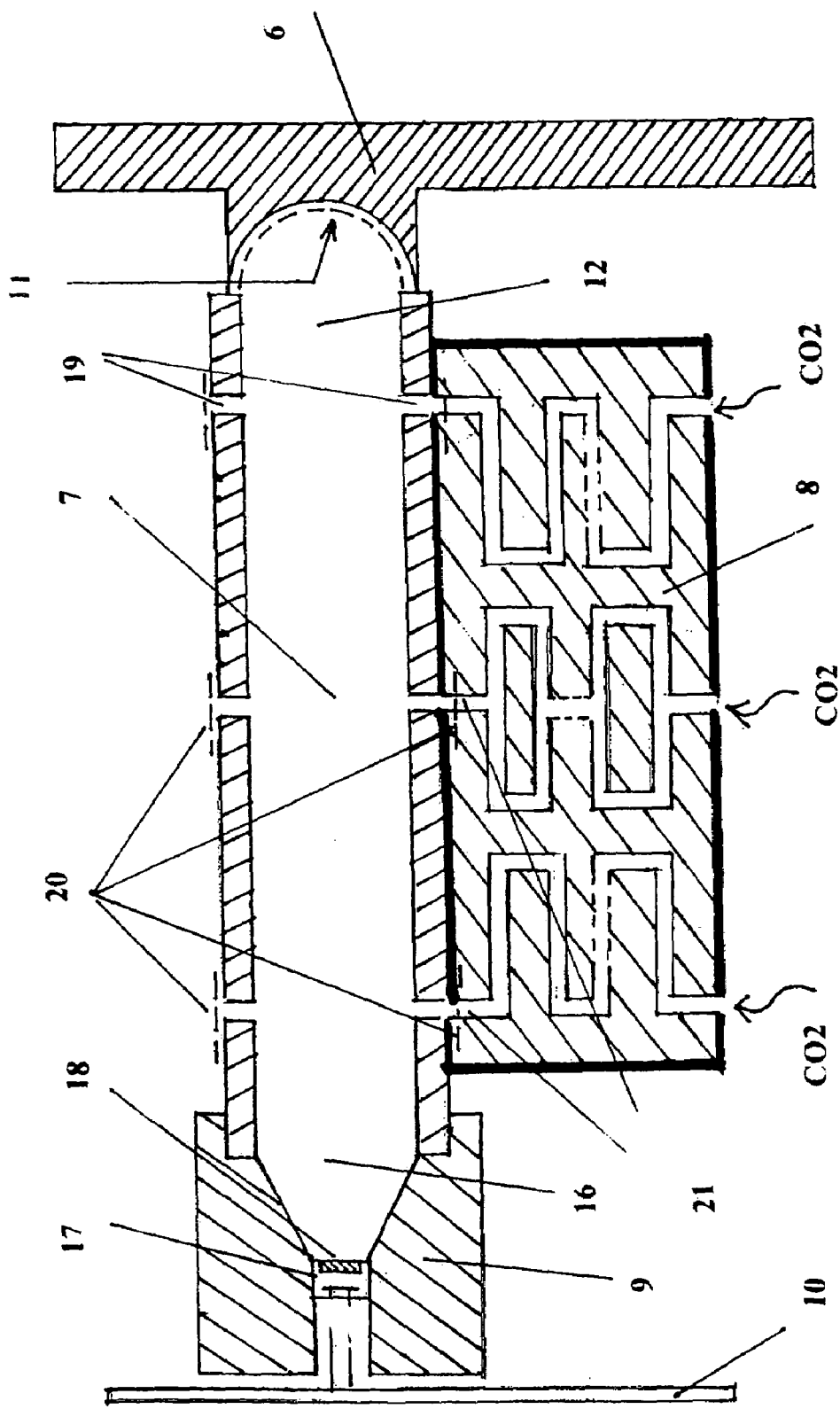
Figure 4. A schematic design and implementation of a passive NDIR CO2 sensor without the use of an active radiation source and deployed as a low power fire detector.

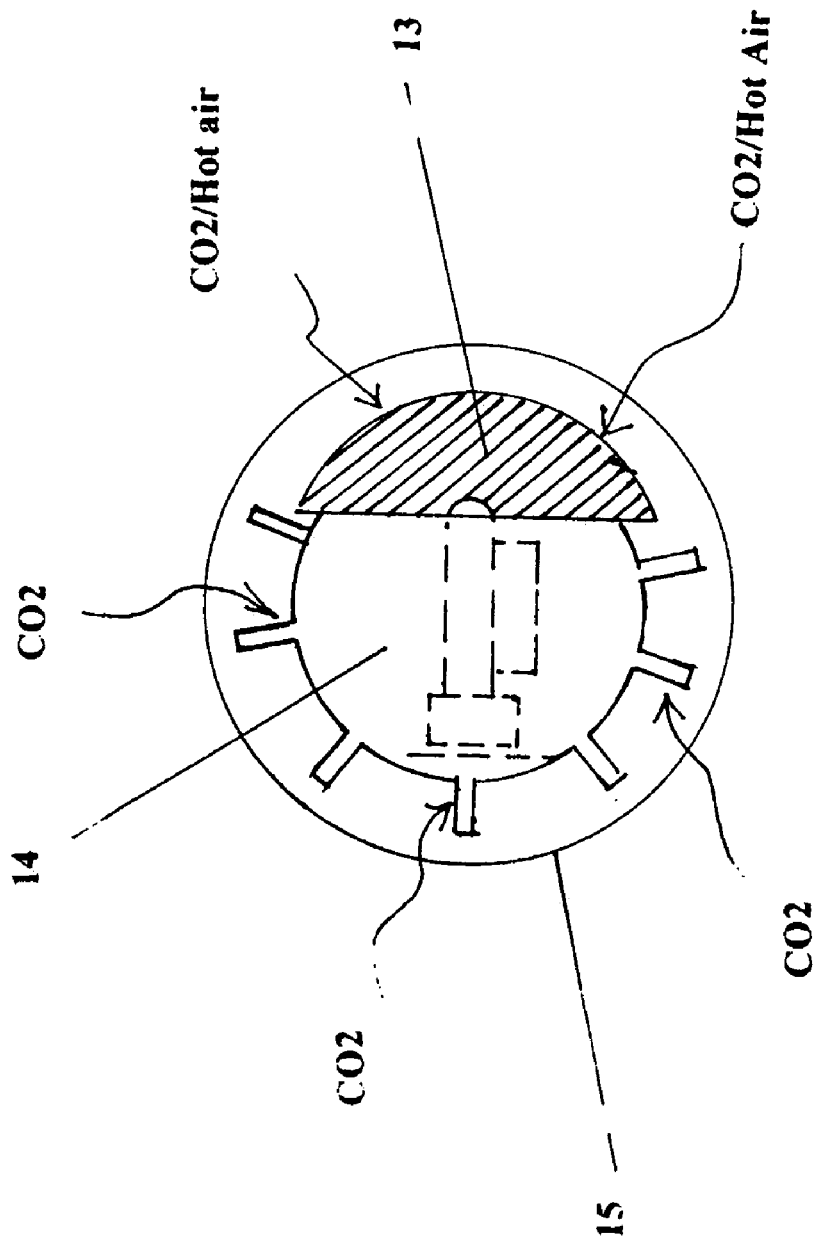
Figure 5. Placement of part of the passive infrared source on the top cover of the fire detector for facilitating the heat transfer with its surroundings.

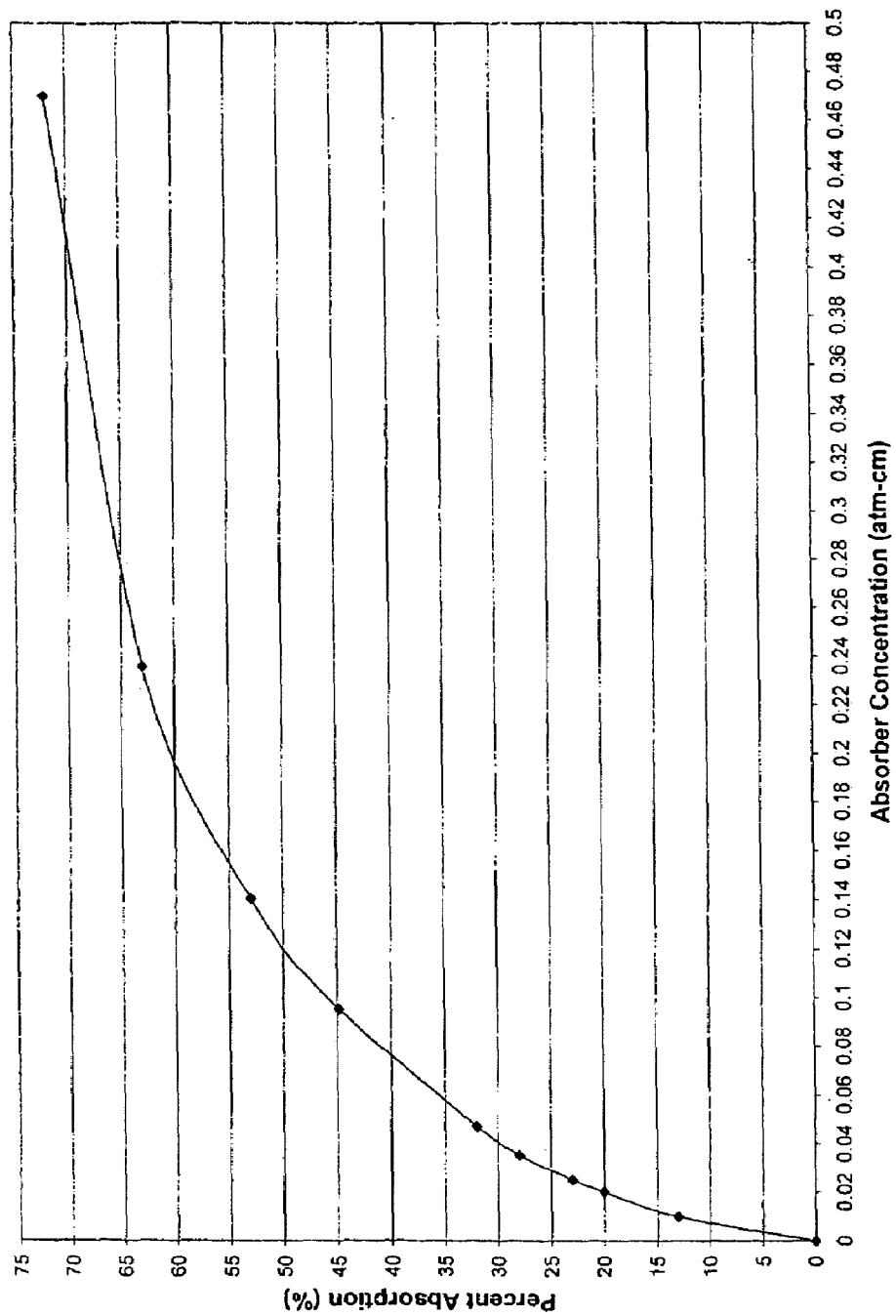
Figure 6. An experimentally measured percent absorption versus absorber concentration curve for the 4.26μ CO2 band with the use of a 0.14μ FWHM spectral filter. Similar results are expected of the ~15μ CO2 absorption band when an 1.0μ FWHM spectral filter is used.

PASSIVE NDIR CARBON DIOXIDE SENSOR FIRE DETECTOR

CROSS-REFERENCE TO RELATED APPLICATIONS

The present application is a continuation-in-part application of U.S. patent application Ser. No. 11/284,460, entitled "Ultra Low Power NDIR Carbon Dioxide Sensor Fire Detector," filed Nov. 21, 2005 with the same inventor, the disclosure of which is specifically incorporated herein by reference.

FIELD OF THE INVENTION

The present invention is in the field of gas analysis and more particularly relates to a passive (no active radiation source used) Carbon Dioxide ($CO_2$) sensor designed to be used as a compact, low power, low cost, fast responding and false alarm resistant fire detector.

BACKGROUND OF THE INVENTION

The Non-Dispersive Infrared ("NDIR") technique has long been considered as one of the best methods for gas measurement. In addition to being highly specific, NDIR gas analyzers are also very sensitive, stable, reliable and easy to maintain. The major drawback of the NDIR gas measurement technique has been its relatively expensive implementation and high power consumption.

Ever since the NDIR technique of gas measurement was first introduced and practiced in the mid 1950's, a large number of improved measurement techniques based upon the NDIR principle for gas detection have been proposed and successfully demonstrated. The most notable advances over the years in this field are summarized as follows.

Burch et al. (U.S. Pat. No. 3,793,525) and Blau et al. (U.S. Pat. No. 3,811,776) in 1974 were the first to advance a so-called "Double Beam" technique for NDIR gas measurement by taking advantage of the principle of nonlinear absorption for some strongly absorbing gases such as $CO_2$ to create a reference channel. Shortly thereafter, this "Double Beam" NDIR gas sensor technique was greatly simplified with the use of two interposed spectral filters (one absorbing and one neutral) to create a sample and a reference detector channel. Subsequent NDIR gas sensors, designed using this technique, have enjoyed good output stability as a function of time.

In U.S. Pat. No. 4,578,762 (1986) Wong advanced the first self-calibrating NDIR $CO_2$ analyzer using a novel two-wheel chopper and mirror arrangement. Another improved type of such gas analyzer is shown and described in U.S. Pat. No. 4,694,173 (1987) by Wong. This gas analyzer has no moving parts for effecting the interposition of spectral filters or absorbing and non-absorbing cells to create both a sample and reference detector channel as in the NDIR gas analyzers described earlier.

In U.S. Pat. No. 5,163,332 (1992), Wong advanced the so-called "wave-guide" sample chamber for simplifying NDIR gas sensors into ones that are compact, rugged and low-cost while still maintaining their superior performance characteristics.

All of the NDIR gas analyzers described above for the measurement of the concentrations of one or more gases in a mixture perform well functionally and have contributed overwhelmingly to the overall technical advancement in the field of gas analysis during the past two decades. They have been widely accepted in both the medical and industrial communities. Despite their undisputed success over the years, there still remain a number of important applications, primarily in the industrial sector, where these NDIR techniques are still too complex, and hence too costly, to be taken advantage of. One such example is the methane gas detector for the miners. The ideal solution here is a small, very low cost and battery-operated methane gas sensor mountable directly below the headlight on the miner's helmet. In the event the miner encounters a methane gas pocket during excavation in the mine, this particular sensor can detect a dangerous level of the gas much sooner than the current setup in which a relatively bulky methane analyzer is normally located quite a distance behind the working miners. Furthermore, such a helmet-mounted methane gas sensor allows the alarm to be placed inside the helmet and close to the miner's ears thereby avoiding the tragic possibility that the alarm from a more remote methane analyzer might be drowned out by the machine noises in the mine.

Another example is the commonplace household fire detector. A majority of fire detectors in use today in almost all public buildings and private dwellings are in essence smoke detectors as they only detect the smoke resulting from a fire. The most common smoke detectors currently in use belong to two types. The first type is the so-called ionization smoke detector best for detecting invisible smoke particles ranging in size from <1.0 microns to ~5 microns. The second type is called the photoelectric smoke detector best for detecting visible smoke particles >5 microns in size. For the past two decades, the ionization smoke detectors because of their low cost (<$10 retail) have dominated the fire market and are in use in over 90% of households. In recent years, photoelectric smoke detectors, because of their higher cost (<$30 retail), have fallen significantly behind in sales. Combined ionization and photoelectric smoke detectors, albeit at an even higher cost (~$40 retail), have also been available for quite sometime but have not to date received much acceptance by the public.

Despite their low cost, relatively maintenance-free operation and wide acceptance by the buying public, the smoke detectors in widespread use today are not without problems and certainly are far from being ideal. One of the biggest problems with ionization smoke detectors besides being radioactive (Americium-241) is their frequent false-alarm. By the nature of its operational principle, any micron-size particulate matter other than smoke from an actual fire can set off the alarm. Kitchen grease particles generated by a hot stove is one classic example. Over-zealous dusting of objects and/or furniture near the detector is another. Frequent false-alarms are not just a harmless nuisance; some people actually disable their smoke detectors by temporarily removing the battery in order to escape such annoying episodes. This latter situation could be outright dangerous especially when these people forget to rearm their smoke detectors.

Another significant drawback for the current ionization smoke detector is its relatively slow speed to alert people of a fire. There are several factors that contribute to this particular drawback. The first fact is the detector trigger threshold for smoke which directly affects its response time to the onset of a fire. No doubt a lower trigger threshold would mean a faster fire detector. However, it also means more frequent annoying false alarms for the user. The second factor is the particular placement of the detector with respect to the spot where fire breaks out. Unlike ordinary gases, smoke is actually a complex sooty molecular cluster that consists mostly of carbon. It is much heavier than air and thus diffuses much slower than the gases we encounter everyday. Therefore, if the detector happens to be at some distance from the location of the fire, it will be awhile before enough smoke gets into the sampling chamber of the smoke detector to trigger the alarm. A third factor is the nature or type of the fire itself. Although smoke usually accompanies fire, the amount produced can vary significantly depending upon the composition of the material that catches fire. For example, oxygenated fuels such as ethyl alcohol and acetone give less smoke than the hydrocarbon from which they are derived. Thus, under free-burning conditions oxygenated fuels such as wood and polymethylmethacrylate give substantially less smoke than hydrocarbon polymers such as polyethylene and polystyrene. As a matter of fact, a small number of pure fuels, namely carbon monoxide, formaldehyde, metaldehyde, formic acid and methyl alcohol, burn with non-luminous flames and do not produce smoke at all.

Since fire is an oxidation process, detection of a sudden increase in ambient $CO_2$ level, one of the three principal effluent gases of fire, is an effective way of detecting same. For the past 20 years, the use of $CO_2$ sensor as a standalone fire detector or in combination with smoke detectors has been continually advocated by experts as the most effective fire detector. The reason is two-fold. First, there is a significant advantage of using a $CO_2$ sensor rather than a smoke detector for fire initiation detection. The mobility of $CO_2$ as a gas is far greater than that for smoke which is much heavier. Therefore $CO_2$ diffuses from the fire to the detector in a much shorter time leading to a faster response time for enunciating fire. Second, over the past two decades, compact, low cost and reliable NDIR type $CO_2$ sensors have become readily available. As a matter of fact, over the same period of time, a large number of deployment schemes, fire fighting techniques and fire control strategies, which use either a standalone NDIR $CO_2$ sensor or in combination with smoke detectors, have been advanced. The most notable proposals of such are summarized as follows.

In U.S. Pat. No. 5,053,754 (1991), Wong advanced the first NDIR $CO_2$ sensor used as a standalone fire detector. A fire detection system using at least two NDIR $CO_2$ sensors positioned at spaced locations in an area for pin-pointing the exact origin of a fire was described in U.S. Pat. No. 5,079,422 (1992) by Wong. Meanwhile a standalone and compact low-cost fire detector which responds quickly to an increase in the concentration of $CO_2$ gas in the ambient air was advanced in U.S. Pat. No. 5,103,096 (1992) by Wong. In U.S. Pat. No. 5,369,397 (1994), an adaptive fire detector taking advantage of the capability of an NDIR $CO_2$ sensor for computing the rate of $CO_2$ increase to shorten the response time for enunciating the onset of a fire was also advanced by Wong. In U.S. Pat. No. 5,592,147 (1997), an NDIR $CO_2$ sensor used cooperatively in combination with a photoelectric smoke detector for significantly reducing false alarms was put forth by Wong. Also in 1997 and in U.S. Pat. No. 5,691,704, Wong disclosed another NDIR $CO_2$/photoelectric smoke detector combination fire detector with special software which can be designed into a single semiconductor chip for cost reduction and further false alarm improvement. In U.S. Pat. No. 5,767,776 (1998), Wong disclosed the design of an NDIR $CO_2$ and smoke detector combination which reduces the maximum average response time to less than 1.5 minutes. Further refinement of this design was described in U.S. Pat. No. 5,798,700 (1998) by Wong, U.S. Pat. No. 5,945,924 (1999) by Marman et al. and U.S. Pat. No. 5,966,077 (1999) by Wong. Finally, a method for dynamically adjusting criteria for detecting fire through smoke concentration using an NDIR $CO_2$ and smoke detector combination was described by Wong in U.S. Pat. No. 6,107,925 (2000).

Despite the continual and persistent advocacy of many fire experts that an NDIR $CO_2$ sensor, either as a standalone fire detector or in combination with a smoke detector, is better than present-day smoke detectors in both speed of response and proof against false alarms, it has yet to be exploited as a superior fire detector. The reasons are two-fold. First, even with the drastic cost reduction for present-day NDIR $CO_2$ sensors, the cost is still far too high when compared with ionization type smoke detectors. Second and by far the most significant is the fact that being an NDIR gas sensor, its active infrared source uses far too much power when operated continuously. Because of this, it is not suitable for use in almost any circumstance, whether it is residential, commercial or industrial. It is therefore the object of the present invention to advance a new design for an NDIR gas sensor aimed at further lowering its cost and, more importantly, reducing its power consumption so that it can in fact be used as a fire detector. It is also an object of the present invention to cater the design of this NDIR gas sensor to be suitable for use as a low power, low cost, false alarm resistant and fast response fire detector.

SUMMARY OF THE INVENTION

The present invention is generally directed to a fire detector that uses a passive $CO_2$ sensor that generates a detector signal based upon a 15μ absorption band of $CO_2$ and a signal processor which receives the detector signal and generates an alarm signal when a preselected criterion is met.

In a first, separate group of aspects of the present invention, the signal processor relies upon a detection algorithm based upon a trending pattern of the detector signal indicative of the onset of a fire, such as a sudden steady increase in the amplitude of the detector signal (converted to a DC signal) caused by rising hot air of a potential fire as the fire first breaks out and may include a substantial drop in the detector signal strength when $CO_2$ subsequently arrives near the sensor as the fire persists.

In a second, separate group of aspects of the present invention, the passive $CO_2$ sensor (which can be used as a standalone smoke detector) has a passive infrared source with a source temperature, a waveguide sample chamber with a gas medium temperature (which is less than the source temperature), a heat exchanger (that reduces the temperature of $CO_2$ gas as it passes into the waveguide sample chamber and may be thermally coupled to the sample chamber) and an infrared detector assembly with a detector temperature (which is less than the source temperature). An exterior surface of the passive infrared source has a high emissivity while the detector assembly and the sample chamber (which can be thermally coupled to each other but not the passive infrared source) have a low emissivity.

In a third, separate group of aspects of the present invention, a fire detector is provided that uses a passive infrared source with a source temperature with a high emissivity that facilitates radiative transfer of heat with an ambient atmosphere, a waveguide sample chamber with a gas medium temperature, a heat exchanger that is thermally coupled to the sample chamber that reduces the temperature of $CO_2$ gas as it passes into the sample chamber, an infrared detector assembly (both the sample chamber and the detector assembly having a low emissivity that does not facilitate radiative transfer of heat with the ambient atmosphere) with a detector temperature that is thermally coupled to the sample chamber and that generates a detector signal based upon a 15μ absorption band of $CO_2$ and a signal processor which receives the detector signal and generates an alarm signal when a preselected criterion is met, the source temperature being greater than either the gas medium temperature or the detector temperature.

In a fourth, separate group of aspects of the present invention, a method for generating an alarm signal in response to a fire uses a passive $CO_2$ sensor to generate a detector signal based upon a 15μ absorption band of $CO_2$ and generates an alarm signal when a preselected criterion indicative of the onset of a fire is met based upon an analysis of the detector signal. $CO_2$ gas is cooled before it enters a sample chamber of the passive $CO_2$ sensor and the temperature of a passive infrared source is greater than the temperature of an infrared detector coupled to the sample chamber which also has a gas medium temperature less than the temperature of the passive infrared source.

It is an object of the present invention to advance a new design for an NDIR gas sensor aimed at further lowering its cost and, more importantly, reducing its power consumption so that it can in fact be used as a fire detector. It is also an object of the present invention to cater the design of this NDIR gas sensor to be suitable for use as a low power, low cost, false alarm resistant and fast response fire detector.

These and further objects and advantages will be apparent to those skilled in the art in connection with the drawings and the detailed description of the preferred embodiment set forth below.

BRIEF DESCRIPTION OF THE DRAWINGS

FIG. 1 is a graph showing the spectral radiant excitance of a blackbody source at temperatures 100–1,0000° K.

FIG. 2 shows the transmittance of the atmosphere for a 6,000 ft horizontal path at sea level showing the presence of the $CO_2$ absorption bands at both 4.26μ and ~15μ.

FIG. 3 shows the absorbance of $CO_2$ gas at wavelengths from ~2μ–20μ (5,000 cm−1–500 cm−1). Only the 4.26μ and ~15μ absorption bands of $CO_2$ are shown to be prominently present in this spectral region.

FIG. 4 shows schematically the design and implementation of a passive NDIR $CO_2$ sensor without the use of an active radiation source and deployed as a low power fire sensor.

FIG. 5 shows the placement of part of the passive infrared source on the top cover of the fire detector for facilitating the heat transfer with its surroundings.

FIG. 6 shows the experimentally measured percent absorption versus absorber concentration curve for the 4.26μ $CO_2$ band with the use of a 0.14μ FWHM spectral filter. Similar results are expected of the ~15μ $CO_2$ absorption band when a 1.0μ FWHM spectral filter is used.

DETAILED DESCRIPTION OF THE INVENTION

Over the past three decades, the design of NDIR $CO_2$ gas sensors has invariably used the strong $CO_2$ absorption band at 4.26μ infrared. This band is not only strong, it is also very specific. In other words, no other gases, other than some extremely weak water vapor absorption continuum, have absorption bands within it. Thus, interferences caused by the presence of other gases to the $CO_2$ measurement are virtually nonexistent. In accordance with the conventional wisdom of NDIR sensor design, the most optimum infrared source to use for $CO_2$ detection should have a blackbody temperature at around 800–900° K, which has its peak spectral radiant excitance located at around 4.26μ according to Planck's Radiation Law. Because of the facts mentioned above, NDIR $CO_2$ sensors are not difficult to design and they were among the earliest NDIR gas sensors manufactured and available for sale to the public circa around mid 1950's. However, the use of a high temperature infrared source for the design of a NDIR $CO_2$ sensor using the 4.26μ absorption band is the main reason why the power consumption for such a sensor is invariably so high and cannot be easily lowered. Since most fire detectors have always been battery-operated, requiring very low power consumption for their continuous operation, this is also the principal reason why NDIR $CO_2$ sensors to date have not found their way to be used as fire detectors.

To overcome this seemingly untenable situation, the present invention uses another specific absorption band for $CO_2$ such that the operating temperature of an infrared source used for its detection can be much lower than that when the 4.26μ absorption band of $CO_2$ is used. Therefore, instead of using the strong 4.26μ absorption band of $CO_2$ to design the sensor of the present invention, the strong and much broader absorption band of $CO_2$ at 14.9–16.2μ is used which shall hereinafter be referred to as the "absorption band at ~15.0μ" or "15μ absorption band of $CO_2$." This 15μ absorption band of $CO_2$ is also very specific. Furthermore, it actually is even slightly stronger than the 4.26μ one.

FIG. 1 shows the graph depicting the spectral radiant excitance of a blackbody source at temperatures 100–1,000° K. The peak spectral radiant excitance for a 800°K blackbody is at 4.26μ which is also the center wavelength (CWL) for the 4.26μ absorption band of $CO_2$ as indicated by the vertical line 1. This confirms the fact that the optimum temperature of the an infrared source using the 4.26μ absorption band for designing an NDIR $CO_2$ sensor is ~800° K. Also shown in FIG. 1 is the Planck's radiation curve for a 300° K blackbody 2, which has a peak spectral radiant excitance at ~10–15μ centering approximately on the 15μ absorption band of $CO_2$. This is the reason why a much lower temperature infrared source can actually be used for the design of an NDIR $CO_2$ sensor when one uses the 15μ absorption band of $CO_2$.

FIG. 2 shows the transmittance of the atmosphere for a 6,000 ft. horizontal path at sea level showing the presence of the $CO_2$ absorption bands at both 4.26μ, 3, and ~15μ, 4. A more quantitative portrayal for these two $CO_2$ bands is depicted in FIG. 3 where the absorbance of $CO_2$ is plotted against wavelength for a gas sample having an absorber concentration of 0.01 atm-cm in Nitrogen and at 1 atmosphere total pressure. One can see from FIG. 3 that these two $CO_2$ bands have roughly the same strength. One can also see from FIG. 3 that with the exception of a couple of weaker bands at ~2.70μ, 5, there are no other $CO_2$ absorption bands present in the spectral region of 2μ–20μ.

While the use of the 15μ $CO_2$ band for the design an NDIR $CO_2$ sensor enables use of much lower temperature infrared sources with values hovering around 300° K, it is even possible to give up the use of an active radiation source altogether and use instead a passive one. By an active radiation source is meant, according to the teaching of U.S. Pat. No. 5,053,754 (1991) by Wong, a miniature conductor that is heated by an electrical current and that emits a spectrum of radiation approximating that of a blackbody source. Thus an active infrared source can assume a number of forms, shapes, sizes and conductive materials. Common active infrared sources include miniature light bulbs, semiconductor resistors, metallic resistors such as nichrome wires, infrared light emitting diodes, etc. Opposite to an active infrared source is a passive infrared source. Although a passive infrared source does not require any electrical current to activate and operates at much lower temperatures, it also emits a spectrum of radiation approximating that of a blackbody. Thus a portion of a wall or ceiling at room temperature $T_0$ is a passive infrared source having a blackbody temperature of $T_0$. A block of wood painted black (emissivity, $\epsilon$, ~1.0) sitting in a room at temperature $T_0$ is also a passive infrared source with a blackbody temperature very close to $T_0$. Without the need to pass electrical current through it in order to activate same, a passive blackbody, as long as it is above absolute zero (0° K) in temperature, spontaneously emits radiation on its own according to the Planck's Radiation law. However, the high range in blackbody temperature for a practical passive source is limited to no more than 300–350° K or 23–77° C. as objects in an environ such as an indoor enclosure seldom exceeds 350° K or 77° C.

Several things need to be heeded before one can successfully use a passive infrared source to design an NDIR $CO_2$ sensor in accordance with the teachings set forth herein.

First, as alluded to earlier, one has to choose the right $CO_2$ absorption band to use with this source. Thus it would be very difficult if not impossible to use the 4.26μ band for designing the NDIR $CO_2$ sensor with a 300° K passive source as the latter has hardly any energy emitted at 4.26μ. On the other hand, the 15μ $CO_2$ band is just about perfect as the peak spectral excitance is located at around the same spectral region for 300° K passive infrared sources. Needless to say one can also use an active infrared source having temperatures of hundreds of degrees Kelvin with the 15μ $CO_2$ band. However, due to the shape of the Planck's Radiation curves, it is highly inefficient and at a diminishing return as the amount of energy available at 15μ for a 800° K active source is only ~10 times more than that for a 300° K passive one.

Second, from the Stefan-Boltzmann Law, the total radiant excitance (W-cm$^{-2}$) of a blackbody source is proportional to the $4^{th}$ power of the absolute temperature T (°K). Thus the total radiant excitance of an 800° K source is $(800/300)^4$ or ~50 times greater than that for an 300° K source. Assuming the detector used is the same for the design of an NDIR $CO_2$ sensor, the S/N will be degraded by the same factor when a passive infrared source (300° K) is used in lieu of an active infrared source (800° K). Thus the performance of the NDIR $CO_2$ sensor cannot be expected to be the same for both cases. The one designed with the active infrared source will perform much better because the sensor S/N is ~50 times better than that designed with the passive infrared source.

Third, and most significant, is to get around the limitation of the Law of Detailed Balance (LDB) which is sometimes called the Zeroth Law of Thermodynamics. Relevant to the present discussion, the LDB sets a detection limitation between an infrared radiator (source) having a temperature $T_s$ (° K) and an infrared detector having a temperature $T_d$ (° K). If the source and the detector are separated by vacuum, there cannot be any signal generated by the detector if $T_d = T_s$. It is however possible if $T_d < T_s$. If the source and the detector are separated by a medium (e.g. cloud of gas) having a temperature $T_m$ (° K), the detector signal cannot see any changes as a result of the presence of the gas cloud as long as $T_m = T_s$. However, if $T_m > T_s$, then the detector can generate a signal due to detecting radiation emitted from the gas cloud. Or if the $T_m < T_s$ and the gas cloud contains one or more infrared absorption bands (e.g. $CO_2$ has absorption bands at 4.26μ and 15μ), then the detector signal will change proportional to the amount of radiation absorbed by the gas cloud. The LDB is important and must be taken into consideration if one deals with passive infrared source having temperatures close to their environ.

We shall now consider the case of a block of wood with its surfaces painted black ($\epsilon$~1.0) and a block of aluminum with highly polished surfaces ($\epsilon$~0.03) being suspended in still air with no or very little contact with surrounding objects except air. Since air is a very poor heat conductor, the principal heat loss or gain for the blocks is through radiation exchange with its surroundings like the walls, floor or ceiling. It is well-known in physics that an object, having an emissivity value approaching unity (blackbody), radiates (loses) heat very efficiently to its surroundings whose temperature is lower. Conversely it also absorbs (gains) heat very efficiently from its surroundings if the latter's temperature is higher. On the other hand, for an object with very low emissivity value, it gains and loses very little heat radiatively to its surroundings if there is a temperature difference. The Law of Detailed Balance (LDB), however, will ensure that as time progresses indefinitely with no physical changes surrounding the blocks except as earlier described, eventually the temperatures of the blocks, irrespective of their large difference in emissivity, will assume the same temperature as their surroundings.

In practice and it is a common experience that a block of highly polished aluminum always feels colder to the touch than a block of wood, especially when the latter is painted black. The reason can be explained by the difference in their emissivity values. During the night when the temperature is colder, both blocks in the course of time will assume about the same temperature as their surroundings as dictated by the LDB. Then as the temperature rises during the day, the block of wood absorbs heat radiatively much more efficiently than the block of polished aluminum and the latter tends to be colder. Although it is very difficult to predict how much colder the block of polished aluminum will be when compared with the block of wood painted black (because it depends on circumstances), it is nevertheless possible, when this fact is combined with the use of the 15μ $CO_2$ absorption band, to design a passive NDIR $CO_2$ sensor specifically deployed as a very low power fire detector.

FIG. 4 shows schematically the design and implementation of such a passive $CO_2$ sensor without the explicit use of a radiation source in order to reduce its power consumption to an absolute minimum. This design comprises five main parts. They are, respectively, a passive infrared source 6, a "waveguide" sample chamber 7, a heat exchanger 8, an infrared detector assembly 9 and signal processing electronics 10. The passive infrared source is essentially a piece of specially shaped wood 6 with a "roughened" semi-spherical cavity 11 facing one end 12 of the sample chamber 7 but thermally decoupled from it. The exterior surfaces of the passive infrared source 6 including the inside "roughened" surface of the semi-spherical cavity 11 are painted with a high emissivity ($\epsilon$>0.95) black paint. The passive source 6 has a special shape having a large protruding surface area 13 exposed to the ambience and forms part of the external top cover 14 of the fire detector 15 as portrayed in FIG. 5. This design facilitates the radiative transfer of heat between the passive source 6 and the ambience due to the high emissivity of the former. Thus the change in temperature of the passive source 6 follows closely with that of its surroundings.

Coupled thermally to the other end 16 of the sample chamber 7 is the infrared detector assembly 9. An infrared detector 17, either thermopile or pyroelectric, is installed in the center of the detector assembly 9 and facing the other end 16 of the sample chamber 7. The infrared detector 17 uses a spectral filter 18 having a CWL=15.1µ and FWHM=1.0µ as its hermetically sealed window. The detector assembly 9 is in essence a highly polished (ε~0.03) aluminum cylinder approximately one inch in diameter and one inch in length with one end opened to accommodate the infrared detector 17 and the other end opened and shaped as a conical mirror for matching the aperture of the sample chamber 7 with that of the detector 17. Sample chamber 7 is an aluminum waveguide or tubing with both its inside and outside surfaces highly polished. Since the sample chamber 7 and the detector assembly 9 are thermally coupled together, their temperatures are very close to one another. As discussed earlier, due to the fact that the emissivities of the passive infrared source and the detector assembly/sample chamber are so much different, the former will assume a slightly higher temperature than the latter. Thus the infrared detector actually generates a very small signal viewing the infrared source with a slightly higher temperature (typically 1–2° C.).

Also coupled thermally to the sample chamber 7 is a heat exchanger 8. The heat exchanger 8 is also made out of aluminum with both internal and external surfaces highly polished. Its temperature therefore follows closely to those of the sample chamber 7 and the detector assembly 9 and is invariably lower than that of the infrared source 6. Along the body of the sample chamber 7 are pairs of openings (holes) 19 covered with a filtering membrane 20 such as a small sheet of polyethylene a few thousandths of an inch thick. These holes allow gases in the vicinity of the sample chamber 7 to diffuse freely into and out of same. However, the filtering membrane 20 covering these openings 19 allows only $CO_2$ gas to do so freely. Anything else such as water vapor, dust, smoke particles etc. would be prevented from entering. Any ambient $CO_2$ gas must first diffuse through the heat exchanger 8 which has matching hole locations 21 with those of the sample chamber 7 (one side only as shown in FIG. 4) before entering the sample chamber 7. As the name implies, the function of the heat exchanger 8 is to cool and lower the temperature of the ambient $CO_2$ gas prior to its entrance into the sample chamber 7 for detection.

The present design of the passive $CO_2$ NDIR sensor deployed as a low power, low cost, fast responding and false-alarm resistant fire detector follows the basic guidelines demanded by the Law of Detailed Balance. First, the design guarantees that the temperature of the passive infrared source 6 (see FIG. 4) is always slightly above that for the infrared detector 17 located within the detector assembly 9. This is achieved by making the source almost a blackbody (ε~1.0) and the detector assembly housing the detector a very poor heat radiator (ε~0.03). Second, in order for the sensor to detect $CO_2$, assuming that the temperature of the gas will equilibrate quickly with that of the sample chamber, the latter must also be cooler than the source. This is achieved by first making the sample chamber 7 a very poor radiator and then thermally decoupling it from the source. Since the sample chamber 7 and the detector assembly 9 have the same goal of making their temperature lower than that of the source, the former can be thermally coupled to the latter as shown in FIG. 4. Third, in order for the detector to sense a difference in the radiation level from the source when $CO_2$ is inside the sample chamber, namely, detect the removal by $CO_2$ of a significant amount of the 15µ radiation emanated from the source, the temperature of the $CO_2$ gas must also be made lower than that of the source according to the LDB. This is achieved with the use of a heat exchanger 8 which is thermally coupled to the sample chamber 7 and hence assumes a lower temperature than that for the source. By making the $CO_2$ gas first pass through the heat exchanger, thereby lowering its temperature to below that for the source prior to entering the sample chamber, its presence can be discerned by the detector as an output signal decrease because of the removal of some of the 15µ radiation it normally receives from the source.

As pointed out before, the current passive NDIR $CO_2$ sensor will not perform as a normally good gas sensor because of its inadequate S/N by virtue of the use of a very low temperature infrared source. The main objective is to render it a very low power fire detector by sensing a sudden and significant rise in $CO_2$ concentration when a fire breaks out. Let us now examine how this fire detector will perform in the event of a real fire for the case of using a thermopile detector. With the exception of a very slow and smoldering fire, the temperature in the vicinity of the fire will invariably rise. The passive infrared source of the present fire detector will be the first to be affected by such a rise in temperature by virtue of its high emissivity. On the other hand, the sample chamber 7, heat exchanger 8 and the detector assembly 9 (see FIG. 4) will only be minimally impacted temperature-wise. Thus the crucial temperature difference between the source and the detector, sample chamber and heat exchanger is maintained. As the fire persists, the $CO_2$ will eventually get to the vicinity of the fire detector. Since it must first pass through the heat exchanger which is by now quite a bit cooler than the passive source, its presence to the detector by ridding off some of the 15µ radiation from the source can now be readily discerned. The detector signal will at first rise slowly due to the increase in temperature of the passive source by virtue of the heat of the fire and then it will drop significantly as the $CO_2$ finds its way into the sample chamber. Thus, by using the trending pattern of the detector output signal, one is able to set a threshold behavior of the output signal for enunciating the onset of a fire.

Essentially the same situation prevails when a pyroelectric detector is used in lieu of a thermopile detector. Since the pyroelectric detector is an AC detector which can only sense a rapid change in the source radiation level, the detector output in the case of a fire will at first stay pretty much zero (no change) despite the slow rise of the passive source temperature due to the heat of the fire. However, when the $CO_2$ finally gets into the sample chamber, there will be quite a significant drop of the detector output since the 15µ absorption band is very strong. FIG. 6 shows an experimentally measured percent absorption versus absorber concentration curve for the 4.26µ $CO_2$ absorption band with the use of a 0.14µ FWHM spectral filter. Although no experimental absorption data is presently available for the 15µ absorption band of $CO_2$, its band strength is slightly stronger than 4.26µ band (see FIG. 3). Assuming that the strength of the 15µ band and the 4.26µ band is the same, a $CO_2$ sample of 2,000 ppm and a path length of 15 cm (designed sample chamber path length), the absorber concentration is $2,000 \times 10^{-6} \times 15$ atm-cm or 0.03 atm-cm, the expected percent absorption of the incident power can be found from FIG. 6 to be ~25% or 0.25. Depending upon the type of fires, the buildup of $CO_2$ is expected to be much higher than 2,000 ppm. Thus the drop in the source radiation level as a result of the presence of $CO_2$ due to the fire can be as much as 25%. Such an AC change in detector output voltage can easily be detected by the pyroelectric detector.

The above paragraphs illustrate the principle of designing an NDIR $CO_2$ sensor deployed specifically as a very low power fire detector using the 15μ absorption band of $CO_2$ but without the use of a radiation source. There are ways to improve the performance of such a low power fire detector. One example is to deploy a longer path length sample chamber in order to increase the detector voltage drop as $CO_2$ appears. One might argue that the current invented fire detector might not be sensitive enough to detect a smoldering fire. However it is worth pointing out the fact that until a smoldering fire eventually breaks out into an open fire, there is hardly any destructive danger associated with it. But before it gets to that point, the ensuing $CO_2$ would have been easily detected and the fire enunciation made. It goes without saying that one of the virtues of deploying the presently invented fire detector is the virtual complete elimination of any false alarm. Furthermore, no longer has one to endure the use of radioactive Americium-214 and its subsequent disposal hazards in using ionization smoke detectors. Thus the previously insurmountable barrier which has long prevented NDIR $CO_2$ sensors from being used as fire detectors because of its high power consumption has now been removed.

While the invention has been described herein with reference to certain examples, those examples have been presented for illustration and explanation only, and not to limit the scope of the invention. Additional modifications and examples thereof will be obvious to those skilled in the art having the benefit of this detailed description. Also, the specific design of a passive $CO_2$ sensor set forth herein can, as already noted, be changed without departing from the key principles and teachings of the present invention, when one begins with the benefits of this disclosure, and many additional modifications are also possible in alternative embodiments without departing from the inventive concept.

Accordingly, it will be apparent to those skilled in the art that still further changes and modifications in the actual concepts described herein can readily be made without departing from the spirit and scope of the disclosed inventions as defined by the following claims.

What is claimed is:

1. A fire detector, comprising:
   a passive $CO_2$ sensor that generates a detector signal based upon a 15μ absorption band of $CO_2$; and
   a signal processor which receives the detector signal and generates an alarm signal when a preselected criterion is met;
   wherein the passive $CO_2$ sensor is further comprised of:
   a passive infrared source with a source temperature;
   a waveguide sample chamber with a gas medium temperature;
   a heat exchanger; and
   an infrared detector assembly with a detector temperature;
   wherein the heat exchanger reduces the temperature of $CO_2$ gas as it passes into the waveguide sample chamber; and
   wherein the source temperature is greater than either the gas medium temperature or the detector temperature.

2. The fire detector of claim 1, wherein the signal processor relies upon a detection algorithm that is based upon a trending pattern of the detector signal indicative of the onset of a fire.

3. The fire detector of claim 2, wherein the detector signal is converted to a DC signal.

4. The fire detector of claim 3, wherein the trending pattern is comprised of a sudden steady increase in the amplitude of the detector signal caused by rising hot air of a potential fire as the fire first breaks out.

5. The fire detector of claim 4, wherein the trending pattern includes a substantial drop in the detector signal strength when $CO_2$ subsequently arrives near the sensor as the fire persists.

6. The fire detector of claim 1, wherein an exterior surface of the passive infrared source has a high emissivity of approximately 0.95 or greater.

7. The fire detector of claim 1, wherein the sample chamber and the detector assembly are thermally coupled.

8. The fire detector of claim 1, wherein the detector assembly and the sample chamber have a low emissivity of approximately 0.03.

9. The fire detector of claim 1, wherein the heat exchanger is thermally coupled to the sample chamber.

10. The fire detector of claim 1, wherein the sample chamber and the passive infrared source are not thermally coupled.

11. The fire detector of claim 1, wherein the passive infrared source has a high emissivity.

12. The fire detector of claim 1, wherein the passive $CO_2$ sensor is used as a standalone smoke detector.

13. A fire detector, comprising:
    a passive infrared source with a source temperature;
    a waveguide sample chamber with a gas medium temperature;
    a heat exchanger that is thermally coupled to the sample chamber that reduces the temperature of $CO_2$ gas as it passes into the sample chamber;
    an infrared detector assembly with a detector temperature that is thermally coupled to the sample chamber and that generates a detector signal based upon a 15μ absorption band of $CO_2$; and
    a signal processor which receives the detector signal and generates an alarm signal when a preselected criterion is met;
    wherein the source temperature is greater than either the gas medium temperature or the detector temperature.

14. The fire detector of claim 13, wherein the passive infrared source has a high emissivity that facilitates radiative transfer of heat with an ambient atmosphere and the sample chamber and the detector assembly have a low emissivity that does not facilitate radiative transfer of heat with the ambient atmosphere.

15. A method for generating an alarm signal in response to a fire, comprising the steps of:
    using a passive $CO_2$ sensor to generate a detector signal based upon a 15μ absorption band of $CO_2$; and
    generating the alarm signal when a preselected criterion indicative of the onset of a fire is met based upon an analysis of the detector signal;
    wherein the passive $CO_2$ sensor is further comprised of:
    a passive infrared source with a source temperature;
    a waveguide sample chamber with a gas medium temperature;
    a heat exchanger coupled to the sample chamber that reduces the temperature of $CO_2$ gas as it passes into the sample chamber; and
    an infrared detector assembly with a detector temperature coupled to the sample chamber that generates the detector signal.

16. The method of claim 15, wherein $CO_2$ gas is cooled before it enters a sample chamber of the passive $CO_2$ sensor.

17. The method of claim 16, wherein the temperature of a passive infrared source of the passive $CO_2$ sensor is greater than the temperature of an infrared detector of said passive $CO_2$ sensor.

* * * * *